United States Patent [19]

Tanaka et al.

[11] Patent Number: 5,434,900
[45] Date of Patent: Jul. 18, 1995

[54] COMPUTED TOMOGRAPHY APPARATUS

[75] Inventors: Shigeru Tanaka, Ootawara; Tsuneto Hiramatsu, Kuroiso, both of Japan

[73] Assignee: Kabushiki Kaisha Toshiba, Kawasaki, Japan

[21] Appl. No.: 87,055

[22] Filed: Jul. 7, 1993

[30] Foreign Application Priority Data

Jul. 8, 1992 [JP] Japan .................. 4-181140
Jul. 31, 1992 [JP] Japan .................. 4-204176

[51] Int. Cl.⁶ .................................... A61B 6/03
[52] U.S. Cl. ........................... 378/15; 378/4; 378/98; 378/207
[58] Field of Search ............ 375/4, 15, 16, 19, 91, 375/102, 110, 112, 204

[56] References Cited

U.S. PATENT DOCUMENTS

| | | |
|---|---|---|
| 3,683,114 | 8/1972 | Egan et al. |
| 4,192,997 | 3/1980 | Baumann .................. 378/15 |
| 4,578,767 | 3/1986 | Shapiro .................. 378/111 X |
| 4,801,803 | 1/1989 | Denen et al. .......... 250/370.01 X |
| 4,853,946 | 8/1989 | Elliott et al. ............ 378/207 X |
| 4,889,991 | 12/1989 | Ramsey et al. ........ 250/370.01 X |
| 4,912,735 | 3/1990 | Beer .................. 378/15 |
| 4,928,283 | 5/1990 | Gordon .................. 378/20 |
| 5,208,581 | 5/1993 | Collins .................. 378/15 X |

*Primary Examiner*—David P. Porta
*Attorney, Agent, or Firm*—Finnegan, Henderson, Farabow, Garrett & Dunner

[57] ABSTRACT

A computed tomography apparatus has a rotating frame unit and at least one of component parts, constituting an X-ray high-voltage generating device, which is mounted on the rotating frame unit. In the apparatus, a signal transmitting section is provided between a rotating frame unit and an outside of the rotating frame unit to transmit a measuring signal at each component part in the X-ray high-voltage generating device. A signal is transmitted by the signal transmitting section between the component part in the X-ray high-voltage section on the rotating frame unit and a device arranged external to the rotating frame unit.

18 Claims, 8 Drawing Sheets

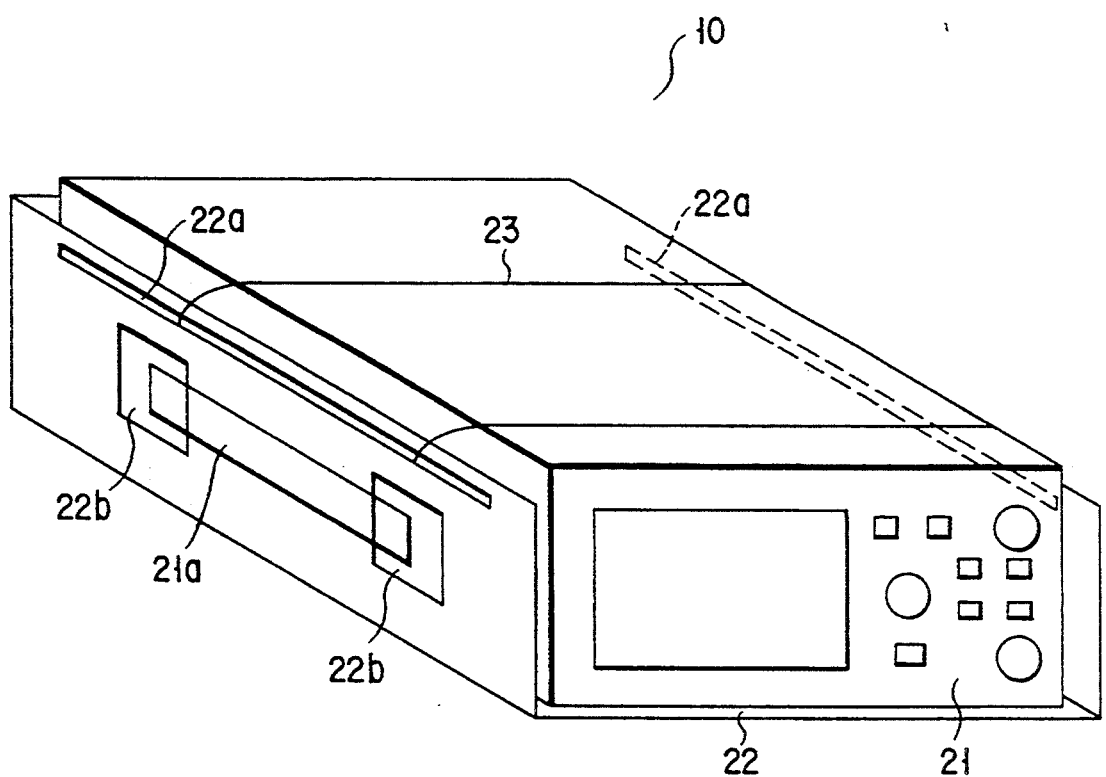
F I G. 3

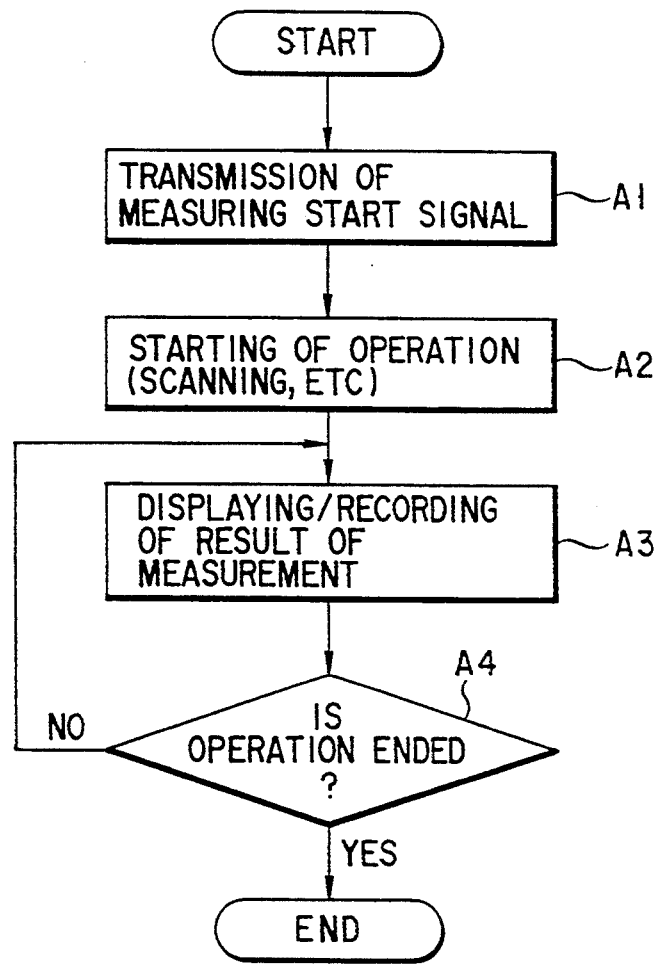
F I G. 4

COMPUTED TOMOGRAPHY APPARATUS

BACKGROUND OF THE INVENTION

1. Field of the Invention

The present invention relates to a computed tomography apparatus such as an X-ray computed tomography apparatus with, for example, an X-ray high-voltage generating device incorporated in a rotating frame unit.

2. Description of the Related Art

An X-ray computed tomography apparatus comprises a rotating frame unit and a fixed section. In that conventional X-ray computed tomography apparatus, those component parts constituting an X-ray high-voltage generating device, such as a high-voltage transformer, inverter and input circuit sections are located at other than the rotating frame unit, for example, at the fixed section and an X-ray tube is placed in the rotating frame unit with a cable, such as a high-tension cable, connected between the X-ray high-voltage generating device and the X-ray tube.

In the case where all those component parts constituting the X-ray high-voltage generating device as set out above are arranged outside the rotating frame unit, the waveforms of the voltage, current, etc., of the X-ray tube can be readily measured, for example, irrespective of whether or not the rotating frame unit is rotated, by measuring the waveform of the high-voltage transformer, etc., of the high-voltage generating device by means of a measuring device. The waveform of each of the component parts constituting the X-ray high-voltage generating device can also readily be measured by means of the measuring device.

In an X-ray computed tomography apparatus of a type in which at least one of its component parts is mounted on the rotating frame unit and an electric power is supplied to the component parts in the apparatus which are mounted by a slip ring on the rotating frame unit, however, it is difficult to measure the waveforms, etc., of the component parts in the apparatus which are mounted on the rotating frame unit and, in particular, difficult to make such a measurement during the rotation of the rotating frame unit.

In the X-ray computed tomography apparatus of an X-ray high-voltage generating device separate type, the X-ray high-voltage generating device is located at a location isolated from an operation room where the apparatus body is placed, that is, at a location where there is no risk of an exposure with an X-ray. In the manufacturing process and service/maintenance checking, the apparatus has its various types of functions controlled by variable resistors, etc., on the board in the apparatus body. The installing of such an X-ray computed tomography apparatus in the medical institution such as hospitals, etc., often has to alter its house/building inner structure in view of a limitation on the mount space, etc., and therefore-the associated equipment has to be fitted for the installation of the apparatus involved.

In view of this limitation an X-ray computed tomography apparatus has been so modified that the apparatus body contains the aforementioned type of X-ray high-voltage generating device including a PC (print circuit) board, etc., and can be installed in a narrower space than before.

In this type of apparatus, the X-ray high-voltage generating device can be checked or adjusted for servicing and/or maintenance (hereinafter referred to simply as the checking, etc.) in the way as set out below.

(1) For safety, the driving unit for the rotating frame unit is turned OFF or that rotating frame mechanism is locked. In this state, various measuring devices (or equipments) are connected to an associated X-ray system circuit for measurement to be carried out.

(2) For protection from an exposure with the X-ray the servicing engineer wears a protective clothing after an X-ray emission outlet has been shielded with a cover.

(3) The X-ray system circuit is switched to a manual control mode by operating a corresponding switch on the PC board.

(4) The tube voltage and tube current mode (X-ray tube) to be adjusted are selected by operating corresponding switches on the PC board.

(5) The tube voltage and tube current are measured through test exposure with the X-ray.

(6) A control variable resistor is adjusted on the PC board.

(7) The tube voltage and tube current are set to their desired value by repeating the steps (5) and (6).

(8) A manual control mode on the X-ray system circuit is switched to a remote control mode. The various measuring devices for measurement are removed and the rotating frame mechanism is unlocked and the frame is turned ON for operation.

Those operations between (1) to (8) are carried out while contacting with the frame.

The conventional X-ray computed tomography apparatus with the X-ray high-voltage generating device incorporated therein encounters the following problems during a manufacturing process and at the adjusting operation of the X-ray high-voltage generating device upon checking for servicing/maintenance.

(1) There is a risk that the servicing engineer will suffer an X-ray exposure when adjusting the X-ray amount upon exposure test.

(2) When the board on the X-ray high-voltage generating device is situated in a rather inaccessible position due to a restriction on the mounting of the X-ray high-voltage generating device relative to the apparatus body, the adjusting operation is both cumbersome and difficult.

(3) Since the apparatus has a rotating section, there is a risk that the servicing engineer will be inadvertently hit by the rotating section during servicing operation.

Further as a system utilizing a signal transmission to the X-ray computed tomography apparatus (hereinafter referred to as an X-ray CT apparatus), a system (hereinafter referred to as a remote diagnostic system) is known which makes a connection, over a telephone line, between the X-ray CT apparatus installed at a site, such as a hospital, and a center side, such as a factory, for the remote control of the X-ray CT apparatus' function for a normal state to be achieved and this is done through a signal transfer of the rotating frame unit to and from an outside source. In the remote diagnostic system, the CT apparatus is normally routinely called from the center side over the telephone line and a diagnostic program on the CT apparatus side is started. A diagnostic examination is carried out, by the diagnostic program, for the normal function of the CT apparatus. The result of diagnostic examination is returned back to the center side again over the telephone line. The center side analytically examines the result of diagnostic examination and determines whether or not there is any abnormal state on the apparatus side. In the center side, the timing for sending a remote command to initiate the diagnostic program is not necessarily set in a routine way and a temporary diagnostic examination can also be carried out when receiving information corresponding to an abnormal state from a staff, for example, an operator and servicing engineers on the hospital side who work directly for operation and checking of the CT apparatus for servicing/maintenance.

However, since, in the conventional remote diagnostic system, the diagnostic program is initiated once any action, being either routine or temporary, is taken on the center side, a longer time period is required until an abnormal state is detected. In the routine diagnostic examination, for example, the diagnostic program is routinely initiated, but, in the event of any abnormal state occurring, a longer time is sometimes passed until the abnormal state is detected. In such a time, no prompt appropriate action can be taken against the occurrence of an abnormal state on the CT apparatus. This involves a continued abnormal state on the X-ray CT apparatus side, thus somewhat adversely affecting a medical action involved. In the temporary diagnostic examination, the center side has to be called, for example, from the hospital's operator, necessarily taking a longer time from the occurrence of the abnormal state to the appropriate action.

SUMMARY OF THE INVENTION

An object of the present invention is to provide a computed tomography apparatus which can measure a signal, a waveform, etc., of each component part constituting an X-ray high-voltage generating device mounted on the drive section and, in particular, on a rotating frame unit of the apparatus, even when the rotating frame unit is rotated.

Another object of the present invention is to provide a computed tomography apparatus which can, for example, freely check a target component part mounted on a scanning body at a location not likely to be exposed with an radiation and so on.

Another object of the present invention is to provide a computed tomography apparatus which can quickly grasp the occurrence of abnormal state in the apparatus, reduce a downtime to a minimum possible extent for prompt recovery and eliminate such an abnormal state from being continued.

The first computed tomography apparatus of the present invention is characterized by a rotating frame unit; an X-ray high-voltage generating device composed of at least one component part mounted on the rotating frame unit; and signal transmission means for allowing a signal transmission to be made between said X-ray high-voltage generating device and external device means arranged outside said rotating frame unit.

Further, the first computed tomography apparatus of the present invention is characterized in that said rotating frame unit has a mount space in which a measuring device is mounted for measuring a signal at each component part of said X-ray high-voltage generating device, or characterized by further comprising a measuring device for measuring a signal at each component part of said X-ray high-voltage generating device mounted on the rotating frame unit.

In addition, the first computed tomography apparatus of the present invention is characterized by a rotating frame unit; and at least one electric device of an optical-system device, a measuring device and data acquisition system mounted on said rotating frame unit, wherein said rotating frame unit has a mount space for mounting a measuring device for measuring a signal at each component part of said electric device, and is characterized by further comprising a measuring device mounted on said rotating frame unit to measure a signal at each component part of said electric device.

According to the first computed tomography apparatus of the present invention, since a means for transmitting a waveform signal, control signal, etc. for maintenance is provided between the rotating frame unit of the apparatus and an outside, for example, a fixed section of the rotating frame unit, it is easier to measure the waveform of, for example, the X-ray high-voltage generating device mounted on the rotating frame unit, particularly the waveform of each component part in the X-ray high-voltage generating means. It is thus possible to make a practical maintenance/servicing operation. Further since it is easier to measure the waveform of each component part in the X-ray high-voltage generating device, it is easier to grasp a cause of a trouble involved, thus ensuring a shorter time of checking for maintenance and servicing. In addition, it can achieve the readiness with which the maintenance/servicing operation is done. As a result, high reliability can be achieved on the present apparatus.

The second computed tomography apparatus of the present invention is characterized by a rotating frame unit; an electric device mounted on said rotating frame unit; an operation mechanism operated in a mount position of said electric device to make at least one of checking and adjustment; signal transmitting means for transmitting a signal to said electric device; and programmable setting means for programmably setting, under remote control, on operation performed by said operation mechanism on said electric device via said signal transmitting means.

According to the second computed tomography apparatus of the present invention, the operating mechanism for making the checking, etc., of the target component parts necessary to do so is connected to the programmable setting means via a communication medium. The programmable setting means can be placed, for example, at a location not likely be exposed with a radiation. The programmable setting means can programmably set, under remote control, an operation (checking, etc.) performed by the operating mechanism on the target component part. It is thus possible to make the automatic checking, etc., of the target component part by the operating mechanism.

.According to the present invention, since the target component part required for the checking, etc., can be programmably so checked under remote control, any adjusting and checking operations can be performed on the target component parts safely and effectively.

The third computed tomography apparatus of the present invention which is installed at a given site and connected to a managing apparatus installed at a center side remote from the site to manage checking of said apparatus for maintenance and servicing through a communication via a telephone line, is characterized by comprising self-diagnosing means included in said computed tomography apparatus for running a diagnostic program related to the checking of a self-function; abnormality determining means for determining the occurrence of any abnormality of the self-function on the basis of a result of diagnosis by said self-diagnosing means; autocall means for automatically connecting a circuit line to the managing apparatus via the telephone line when said abnormality determining means determines a presence of the abnormality; information transferring means for transferring the result of diagnosis by said self-diagnosing means and result of determination by said determining means to said center side via the telephone circuit when the telephone line is connected by said autocall means; and servicing command informing means for sending a command for a servicing action on the abnormality in said apparatus, on the basis of information transferred from said information transferring means.

According to the third computed tomography apparatus of the present invention, the self-diagnosing means per se executes the diagnostic program at a proper timing on the apparatus side and checks the self-function. Based on the result of diagnosis, the determining means determines the occurrence of the abnormality of the self function and, when it determines the presence of the abnormality, the autocall means is operated to enable the telephone line to be automatically connected via the telephone line to the managing apparatus on the center side. When the circuit line is connected by the autocall means, the information transferring means transfers the result of diagnosis by the self-diagnosing means and result of determination by the determining means to the managing apparatus via the telephone line. The servicing command informing means on the managing apparatus sends a command for a servicing action against the abnormal state, such as the supply of component parts required in that case.

According to the third computed tomography apparatus of the present invention, the computed tomography apparatus, such as the X-ray computed tomography apparatus installed at the site is connected via the telephone line to the managing apparatus installed at the center side for communication. The diagnostic program on the checking of the self-function is run on the computed tomography apparatus side and the functional abnormality is determined based on the result of determination. If the abnormal state is determined as being present, the circuit line is automatically connected to the managing apparatus via the telephone line and, at the same time, the result of self-diagnosis and result of that determination are sent to the center side via the telephone line. A command for the servicing action on the abnormal state of the computed tomography apparatus is sent to the managing apparatus side. For this reason, without the need for the starting of the diagnostic program from the center side and the informing of the operator's information from the site side to the center side, the computed tomography apparatus starts the diagnostic program, enabling the abnormality of the tomography apparatus to be rapidly grasped so that any abnormal state can be promptly recovered. It is possible to reduce the downtime of the tomography apparatus and effectively operate the apparatus. It is thus possible to restrict any delay or other adverse effect on the medical action to a minimum possible extent.

According to the third computed tomography apparatus of the present invention, the abnormality determination means determines the occurrence of the functional abnormality when the abnormal state occurs during normal operation of the computed tomography apparatus, and the autocall means may start and automatically connect the circuit line to the managing apparatus of the center via the telephone line.

The servicing command informing means of the managing apparatus side may command to the service station if necessary.

Additional objects and advantages of the present invention will be set forth in the description which follows, and in part will be obvious from the description, or may be learned by practice of the present invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the present invention in which:

FIG. 3 is a view showing the example for an oscilloscope mounted on a rotating frame unit as a measuring device;

FIG. 4 is a flow chart showing the flow of measurement done in the apparatus;

DETAILED DESCRIPTION OF THE PREFERRED EMBODIMENTS

A computed tomography apparatus according to the present invention will be explained below with reference to the accompanying drawings.

Although being explained as being limitative on an X-ray CT apparatus, the present invention is not restricted thereto and can be applied to a computed tomography (CT) apparatus.

Figure 1:
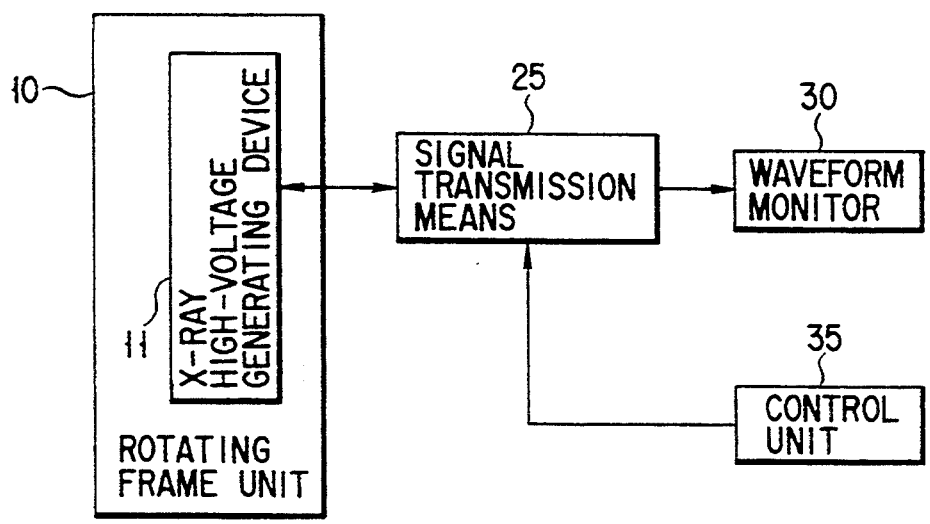
FIG. 1 is a diagrammatic view showing an X-ray CT apparatus according to a first embodiment of the present invention.

FIG. 1 is a view schematically showing an arrangement of an X-ray CT apparatus according to a first embodiment of the present invention.

The X-ray CT apparatus comprises a rotating frame unit (a driving unit) and a remaining section, for example, a fixed section. In FIG. 1, the rotating frame unit 10 has an X-ray tube, measuring devices, etc., not shown, mounted thereon and is adapted to receive a to-be-diagnosed object at its center area. A diagnostic examination is made through X-ray exposure to the object. An X-ray high-voltage generating device 11 is mounted on the rotating frame unit 10 in the present X-ray CT apparatus. The X-ray high-voltage generating device 11 is connected via a signal transmitting means 25 to a waveform monitor 30 and control section 35 external to the rotating frame unit 10. The X-ray high-voltage generating device 11 basically comprises a high-voltage transformer, an inverter and an input circuit section. In the present embodiment, all component parts in the X-ray high-voltage generating device may be mounted on the rotating frame section 10 or some component part, for example, the high-voltage transfer only, may be mounted on the rotating frame unit 10.

In an explanation given below, an assumption is made that all the component parts in the X-ray high-voltage generating device are mounted on the rotating frame unit 10.

In the arrangement shown above, a signal waveform or a signal (hereinafter referred to as the waveform) of the X-ray high-voltage generating device 11 on the rotating frame unit of the X-ray CT apparatus is delivered via the signal transmitting means 25 to the waveform monitor 30, enabling the waveform to be readily observed. Based on the result of observation on the waveform monitor 30 the control unit 35 transmits a corresponding signal via the signal transmitting means 25 to the X-ray high-voltage generating device 11 for waveform adjustment, etc.

Since the signal transmitting means 25 is provided between the rotating frame unit 10 and its outside, even if the rotating frame unit 10 is being rotated, it is possible to readily observe the waveform of the X-ray high-voltage generating device 11 on the rotating frame unit 10 and to easily perform an adjustment in the case where that waveform is abnormal. In the X-ray CT apparatus with the X-ray high-voltage generating device mounted on the rotating frame unit 10, it is considered advantageous to measure the current and voltage of the X-ray tube during rotation of the rotating frame unit 10 as well as the waveform at each component part of the X-ray high-voltage generating device.

Figure 2:
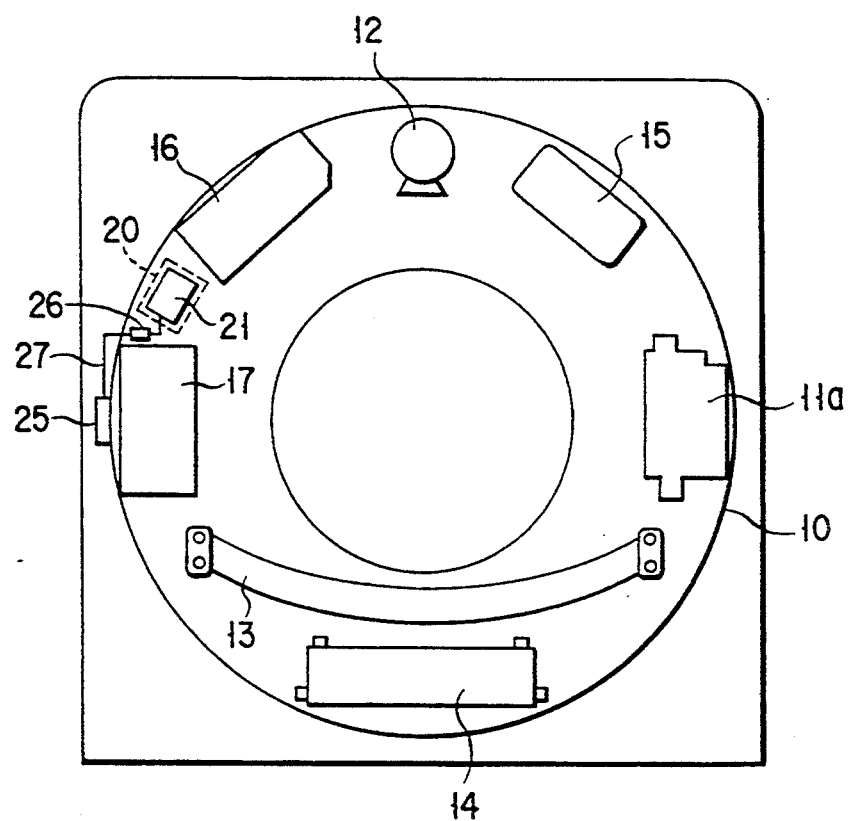
FIG. 2 is a view showing a measuring device, etc., mounted on a rotating frame unit in the apparatus.

FIG. 2 is a detailed view showing a measuring device 21, such as an oscilloscope, and X-ray high-voltage generating device 11 mounted on the rotating frame unit 10 in FIG. 1. In FIG. 2 the same reference numerals are employed to designate parts or elements corresponding to those shown in FIG. 1 and any corresponding detailed explanation is, therefore, omitted for brevity's sake.

In the arrangement shown in FIG. 2, the measuring device 21 is mounted on the rotating frame unit 10, thus eliminating the need to provide the waveform monitor 30 shown in FIG. 1. It is only necessary, in this case, to provide a display unit for displaying a waveform involved. In FIG. 2, especially in the CT apparatus mounting the X-ray high-voltage generating device, since a mounting space to mount such as an inverter unit 16, a converter unit 17 and high-voltage transformer 11a is necessary, a mounting density is high.

In order to tolerate the rotating force of the rotating frame unit 10, a layout mounting design of the CT apparatus is necessary on condition that a mounting space is secured or a device is mounted. For example, by mounting the measuring device shown in FIG. 2, it becomes easier to connect to such as inverter unit 16 and converter unit 17 which are necessary to observe a waveform especially at the time of maintenance and so On.

In the X-ray CT apparatus shown in FIG. 2, a mount space 20 for the mounting of the measuring device 21, etc., is provided in the rotating frame unit 10. The measuring device 21 is provided in the mount space 20 and a high-voltage transformer 11a, an X-ray tube 12, an detector 13, a DAS 14, an oil cooling unit 15, inverter unit 16, converter unit 17, and transmission connector 26 are arranged in other places.

The measuring device 21 is connected by a signal transmission line 27 to the transmission connector 26. The transmission connector 26 and measuring device 21 are connected to the inverter unit 16 and converter unit 17 by a signal transmission line 27. The high-voltage transformer 11a is connected to the X-ray tube 12 by a high-tension cable (not shown). An electric power is supplied by a power source cable, not shown, to the high-voltage transformer 11a and it is supplied by a slip ring, not shown. The transmitting connector 26 a signal transmission to be made to an external device of the rotating frame unit 10 via a signal transmitting means 25.

In the CT apparatus mounting X-ray high-voltage generating device, since the mounting density becomes high, it is difficult to secure mounting space of the measuring device. By preparing the mounting space of the measuring device, it becomes easier to connect to, for example, such as the inverter unit 16 which are necessary to observe a waveform.

Specifically, FIG. 3 shows an example for an oscilloscope is mounted on the rotating frame unit 10 as a measuring device.

In FIG. 3, a measuring device attaching box 22 is fixed to the rotating frame unit 10. The oscilloscope 21 is fixed by a belt 23 furnished to the holes bored in the both upper sides of the measuring device attaching box 22. In addition, a hole 22b for a belt 21a of the measuring device 21 is bored in one side of the measuring device attaching box 22.

The operation of the present apparatus thus arranged will be explained below.

The measuring device 21 starts a measuring operation by the external control section 35 via the signal transmitting means 25 such as a light transmitting means. When an X-ray tube 12 irradiates an X-ray with the rotation of the rotating frame unit 10, then a signal from a corresponding respective component part in such as the X-ray high-voltage generating unit 11 is input to the measuring device 21 via a signal cable, not shown. The waveform obtained at the measuring device 21 for measurement is output to the external device (for example, waveform monitor 30) of the rotating frame unit 10 via the transmission connector 26 and signal transmitting means 25 for waveform measurement to be made.

If any abnormal waveform is detected upon measurement, the control unit 35, such as a personal computer, delivers a control signal via the signal transmitting means 25 and signal transmission connector 26 to the X-ray high-voltage generating device 11 to enable control to be made as will be set out in more detail below.

Further the waveform obtained at the measuring device 21 is sent to the external device of the rotating frame unit 10 via the signal transmitting means 25 so that the monitoring of a measured waveform by the waveform monitor 30, the displaying of a result of measurement on the monitor of the personal computer and not only the aforementioned waveform measurement but also the transferring of data can be carried out. The X-ray high-voltage generating device 11 can be externally controlled by monitoring the waveform involved, etc.

According to the present invention, even during the rotation of the rotating frame unit 10, maintenance information such as a waveform at each component part of the X-ray high-voltage generating device on the rotating frame unit 10 can readily be output to the external device such as the waveform monitor 30, etc., on the rotating frame unit 10 and, as will be set out below in more detail, it is possible to control the X-ray high-voltage generating device 11 from the external device such as the control unit 35.

By the arrangement as set out above, the waveform can be measured even during the rotation of the rotating frame unit 10 and the X-ray high-voltage generating device, etc., can perform substantially the same measurement just as the fixed system arranged at a site separate from the rotating frame unit 10 can do so.

Further during an exposure with the X-ray the operator can measure a signal from each component part of the X-ray high-voltage generating device on the rotating frame unit 10, without being exposed to the X-ray, by extending a signal transmission line 27 of the signal transmitting means 25 to an operation room. By connecting the signal transmission line 27 of the signal transmitting means 25 to a console (operation panel) of the CT apparatus signal transmission can be made through the utilization of the console's keyboard, monitor, etc.

It is considered particularly advantageous to apply the present invention to an X-ray CT apparatus of such a type as to mount the X-ray high-voltage generating device 11 (or an X-ray control unit 40) on the rotating frame unit 10. The X-ray CT apparatus of the present invention can stably monitor the waveform of the X-ray high-voltage generating device 11 on the rotating frame unit 10, in particular, the waveform of each component part of the X-ray high-voltage generating device 11, or confirm the voltage and current of the respect part above, irrespective of whether or not the rotating frame unit is rotated or irrespective of whether or not the X-ray is irradiated.

Although, in the aforementioned embodiment, the X-ray high-voltage generating device 11 has been explained as being mounted on the rotating frame unit 10, the present invention can be applied irrespective of whether or not the device 11 is mounted on the rotating frame unit 10, and can also be applied to the transmission/reception of control signals of component parts in an optical system, such as a collimator, wedge, etc., mounted on the rotating frame unit 10 or to the monitoring of an external waveform of other devices.

The present invention can also be applied to monitoring the signal and wavelength of the measuring device and data acquisition system (DAS) and to readily confirming an abnormal state heretofore impossible to do so, and can contribute much to shortening a maintenance time and giving added safety to the apparatus obtained.

FIG. 4 is a flow chart showing the measuring process of the X-ray high-voltage generating device 11 on the apparatus shown in FIG. 1.

First, the measuring device is set by the control unit 10 and a measuring start signal is transmitted (step A1). An operation, such as scanning, is started at step A2. A result of measurement, such as waveform data, during the operation of the apparatus, is supplied to the waveform monitor 30. A predetermined processing, such as the displaying, recording, etc., of data, is performed on a computer, etc., not shown (step A3). The present operation is completed at step A4 after all the associated operations have been completed.

As described above, it is possible to measure the characteristics, such as the current, voltage, etc., of the X-ray high-voltage generating device 11 on the rotating frame unit 10. Step A3 in FIG. 4 also outputs a signal to the X-ray high-voltage generating device 11 on the rotating frame unit and controls the X-ray high-voltage generating device 11.

Figure 5:
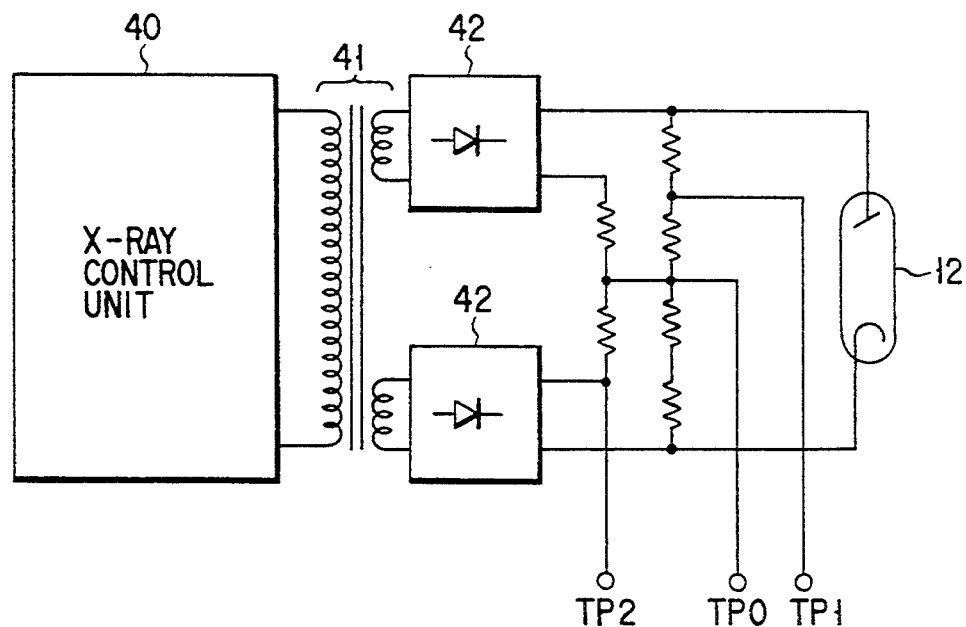
FIG. 5 is a circuit diagram showing a signal taking arrangement.
Figure 6A:
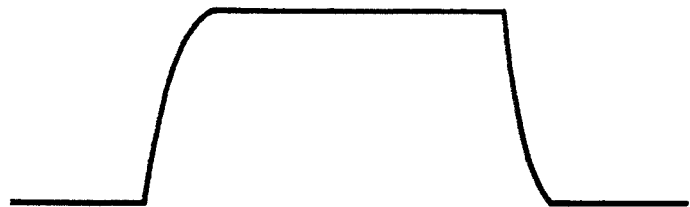
FIGS. 6A and 6B are waveform diagrams of signals taken out of the circuit shown in FIG. 5.
Figure 6B:
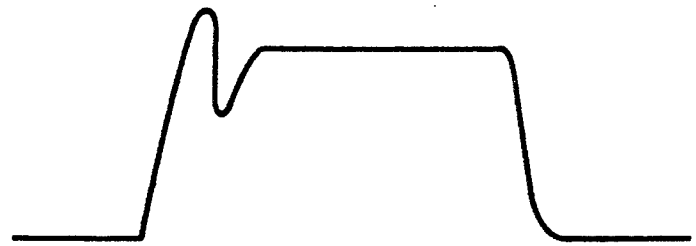

Taking out a signal and observing the waveform involved will be explained below in more detail with reference to FIGS. 5, 6A and 6B. FIG. 5 is a circuit diagram showing these parts for waveform observation in the case where a high voltage is applied to the X-ray tube 12; and FIGS. 6A and 6B are waveforms taken out from the corresponding circuit parts in FIG. 5. Here it is assumed that the circuit parts are all mounted on the rotating frame unit 10.

In the circuit shown in FIG. 5, an output of an X-ray control unit 40 is converted by a high-voltage transformer 41 to a voltage and rectified by a rectifier 42 and applied to the X-ray tube 12 where a corresponding X-ray is generated.

In the case where, for example, the voltage and current of the X-ray tube 12 are to be monitored, the measurement of the X-ray high-voltage generating device 11 is carried out by initially setting test points on a bleeder output and a detection point corresponding to a neutral point current as shown in FIG. 5 and connecting an oscilloscope probe to a corresponding point. A result of measurement is output by the signal transmitting means 25 to the external device on the rotating frame unit 10 whereby it is possible to readily observe the waveform of any desired part on the circuit.

For example, an anode-side tube voltage can be monitored if the probe is connected across the points TP1 and TP0 and a cathode-side neutral-point current (tube current) can be monitored if the probe is connected across the points TP2 and TP0. This measurement can readily be made across the cathode and the anode through a specific arrangement of a circuit such as an operational amplifier.

Observing the waveforms by the waveform monitor 30 as shown in FIGS. 6A and 6B, for example, will be explained below.

In the case where a waveform across the points TP2 and TP0 as shown in FIG. 6B are monitored on the waveform monitor 30 with a waveform set across the points TP2 and TP0 as shown in FIG. 6A, a result of observation is displayed or recorded. If necessary, a signal from the external device such as the control unit 35 is output to the X-ray control unit 40 so that the waveform as shown in FIG. 6B is measured. According to the present invention the output waveform of the X-ray high-voltage generating device 11 on the rotating frame unit 10 can be observed readily from outside the rotating frame unit 10 and, if the waveform is not a desired one, it is possible to readily adjust that waveform from outside the rotating frame unit 10.

If a clamping type current probe is connected to the oscilloscope, it is possible to readily monitor the current waveform of each part of the circuit above. Similarly, if those test points are initially provided, then it is possible to readily measure a control waveform, etc. Even if any test points are absent, the oscilloscope probe can be used for test connection and a similar test connection can be achieved if a current probe is properly inserted.

When the frame is stopped (not rotated), it is possible to make measurement with the use of a separate oscilloscope, but measurement cannot be done during the rotation of the frame. It is considered advantageous, according to the present invention, to monitor the tube voltage, current, etc. upon scan, that is, while an exposure is being made with the X-ray during the rotation of the rotating frame unit 10.

Although, in the first embodiment, the light transmitting means has been explained as being the signal transmitting means 25, if the signal transmission is to be made by light transmission, a maintenance signal line can be secured, through signal multiplexing, without incurring so much cost. Even in the case where not only the light transmitting means but also the slip ring is employed as the signal transmitting means 25, a similar thing can be achieved, through signal multiplexing, in the same way as the light transmission.

Further, as the signal transmitting means 25 use may be made of not only the light transmission or slip ring, but also the spatial transmission of an electromagnetic wave and light for instance. Using, for example, RS-232C, GP-IB, etc., as the signal transmitting means 25 it is possible to achieve not only the control of the measuring device 21 but also the transmission of a waveform. The present invention is not restricted to the use of the RS-232 or GP-IB signal and, as the case may be, can be applied to the direct transmission of an analog signal or to the transmission of a digital signal to which an analog replica is A/D converted.

The data transmitted by the signal transmitting means 25 can of course be reserved as data as set out above. The transmission data can be utilized, by the external device for the rotating frame unit 10, such as the console and computer, when comparison is made between normal and abnormal data.

The measuring device (oscilloscope, etc.) 21 may be mounted on the rotating frame unit only upon maintenance or be normally mounted on the rotating frame unit. Various types of measuring devices can be employed as the measuring device 21, such as a tester, voltmeter, ammeter, tube voltmeter, tube ammeter and dosimeter. Further the measuring device 21 is not restricted to any commercially available one and, if having a measuring function, may be incorporated into the apparatus or constitute part of the apparatus.

In addition, the measuring device is made of a single measuring device or replaced with a plurality of such measuring devices in which case these measuring devices may be switchingly used or be remounted for measurement.

The first embodiment as set out above has been explained in connection with observing the signal of the device, etc., of the X-ray high-voltage generating device on the rotating frame unit which is taken out of the rotating frame unit. Further in the first embodiment the measuring device per se has been explained as being mounted on the rotating frame unit or in the mount space.

Explanation will be given below of a second embodiment of the present invention which controls an electric device such as the X-ray high-voltage generating device, etc., on the rotating frame unit from outside the rotating frame unit.

Figure 7:
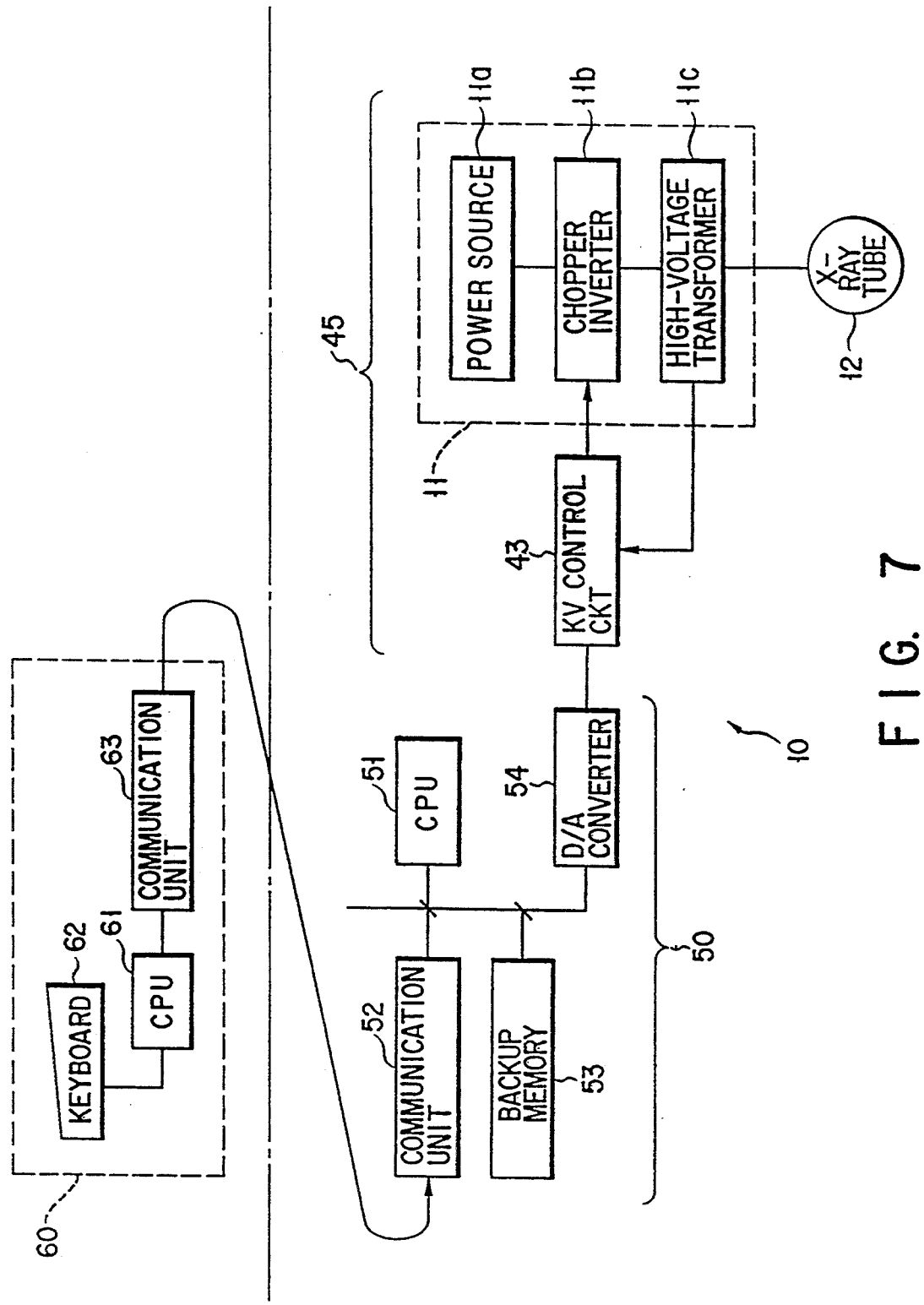
FIG. 7 is a block diagram showing an X-ray CT apparatus according to a second embodiment of the present invention.

FIG. 7 is a block diagram showing an X-ray CT apparatus according to the second embodiment of the present invention.

As set out in connection with the first embodiment, the X-ray CT apparatus has an X-ray high-voltage generating device 11 containing a power source 11a, chopper/inverter 11b and high-voltage transformer 11c on the rotating frame unit 10 arranged, for example, in the operation room. If, therefore, a checking operation, etc., is done at an area exposed with an X-ray coming from an X-ray tube or at an adjacent area, then there is a risk that the operator will be exposed with an X-ray. If, on the other hand, the board of the X-ray high-voltage generating device 11 is located in a somewhat inaccessible place from the standpoint of a limitation on the mounting of the X-ray high-voltage generating device on the rotating frame unit 10, it is difficult to perform an adjusting operation on the board of the X-ray high-voltage generating device 11. Further, since the rotating frame unit 10 is rotated, there is a risk that the operator will touch the rotating frame unit 10 during operation.

In the second embodiment, an X-ray system circuit 45 containing, together with the X-ray high-voltage generating device 11, a kV control circuit 43 for checking the X-ray high-voltage generating device 11 is mounted on the rotating frame unit 10 and a kv detection signal for detecting a current (tube current) and voltage (tube voltage) applied from the high-voltage transformer 11c to the X-ray tube 12 is fed back to the kv control circuit 43. A computer board 50 is provided on the X-ray CT apparatus body or at an area near to the apparatus body. The computer board 50 has a CPU51, serving as a control center, a communication unit 52, backup memory 53 and D/A converter 54. By reading out backup data from the backup memory 53 and, after being converted by the D/A converter 54 to a kV reference output signal, applying the kV reference output signal to the kV control circuit 43, CPU51 can, for example, check the X-ray system circuit 45.

A console 60 comprises a CPU61, serving as a control center, a keyboard 62 and communication unit 63 and are installed at a location not likely to have the operator exposed with the X-ray, that is, at a location remote from the rotating frame unit 10 or remote from the operation room.

The communication unit 52 in the computer board 50 is connected to the communication unit 63 in the console 60 to allow communication therebetween. By the operation of the keyboard 62 on the console 60, the operation such as checking, etc., of the X-ray system circuit 45 by the computer board 50 can be programmably set under remote control.

Figure 8:
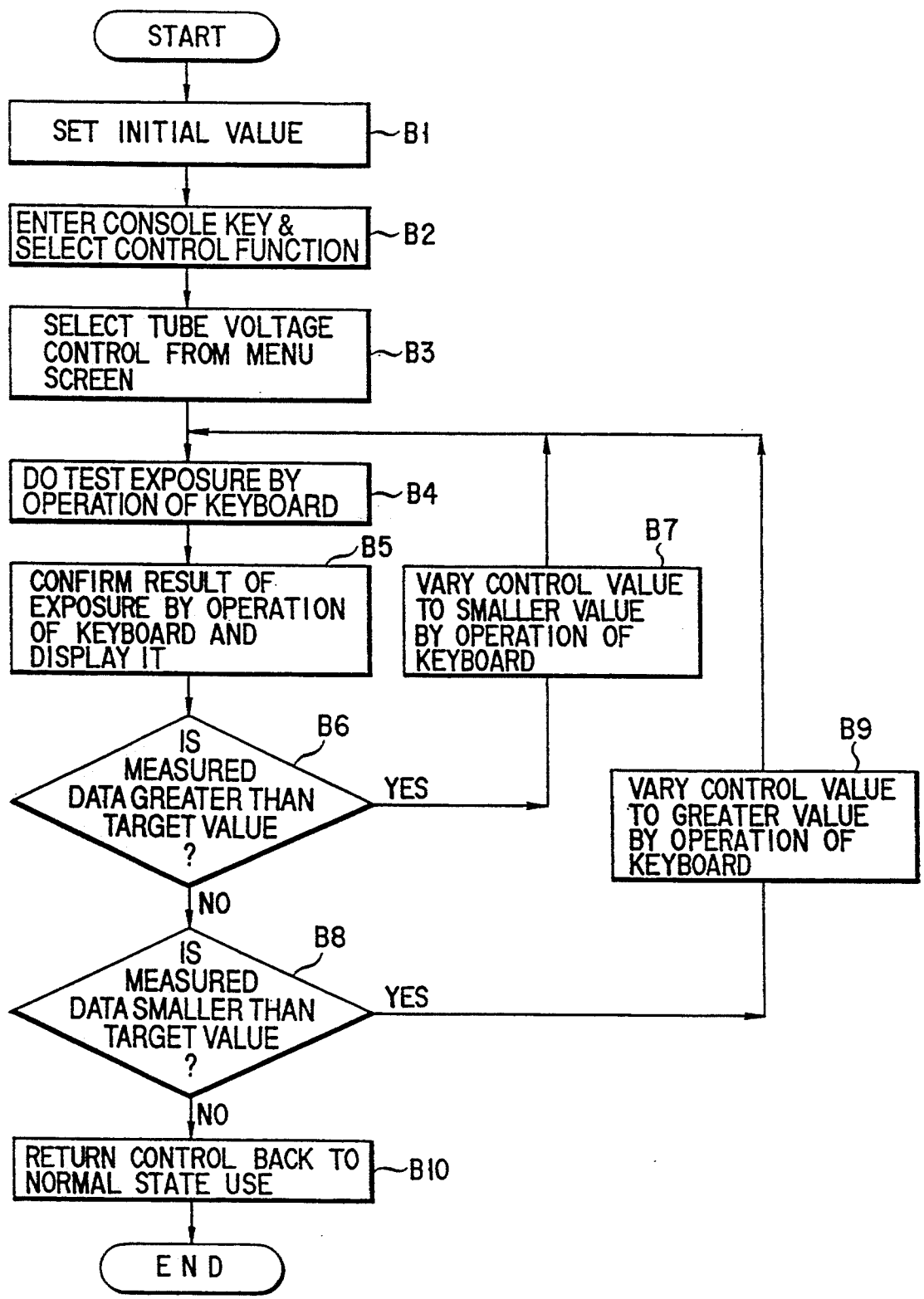
FIG. 8 is a flow chart showing an example of operations at a console of the apparatus.

In the present embodiment, a power source for the rotational operation of the frame is turned OFF, or the rotating frame mechanism is locked, for a safety purpose as set out above. If, in this state, an electric power is supplied to the system with various measuring devices connected to associated parts, then the operation, such as checking, etc., can be performed on the console, as set out below, in accordance with a flow chart shown in FIG. 8.

The system's power source is turned ON at step B1. A key-in operation is made on the console 60 and the control functions of the tube voltage, tube current, etc., are selected at step B2. After the control function has been so selected, the tube voltage control, for example, is selected from a menu screen at step B3. Upon keyboard operation for test exposure, the content of the operation is transferred from the console 60 to the computer board 50 and stored in the backup memory. The X-ray system circuit 45 is responsive to data read out of the backup memory and drives the X-ray system circuit 45 and a test exposure is done at the X-ray tube 12 (step B4). After the test exposure has been done, when the key board is operated so as to confirm the result of the test exposure, corresponding measuring data from the various measuring devices are displayed on the screen (step B5).

When the measuring data on the screen is greater than a target value (step B6), the keyboard is operated to input adjusting data as a smaller one so as to vary the corresponding content of the backup memory (step B7) for another test exposure to be carried out (step B4). When, on the other hand, the measuring data on the screen is greater than the target value (step B8), the keyboard is operated to input adjusting data as a greater one so as to vary the corresponding contents of the backup memory (step B9) for a test exposure to be carried out (step B4). When the measuring data on the screen reaches a target value, control is returned back to a normal state of use (step B10). When the measuring data coincides with the target value at the first test exposure (step B4), control is ended simply by checking.

Although the second embodiment has been explained in conjunction with only a diagnostic examination with the exposure made with the X-ray, the present invention is not restricted thereto. The present invention can also be applied to, for example, a diagnosis on the rotation state of the rotating frame unit and on the state of an up/down motion on a fed or state of sliding on a top plate. That is, the second embodiment can be applied to diagnosing the measurement on the rotation speed of a frame, the movement of the top plate to a designated position, etc.

Figure 9:
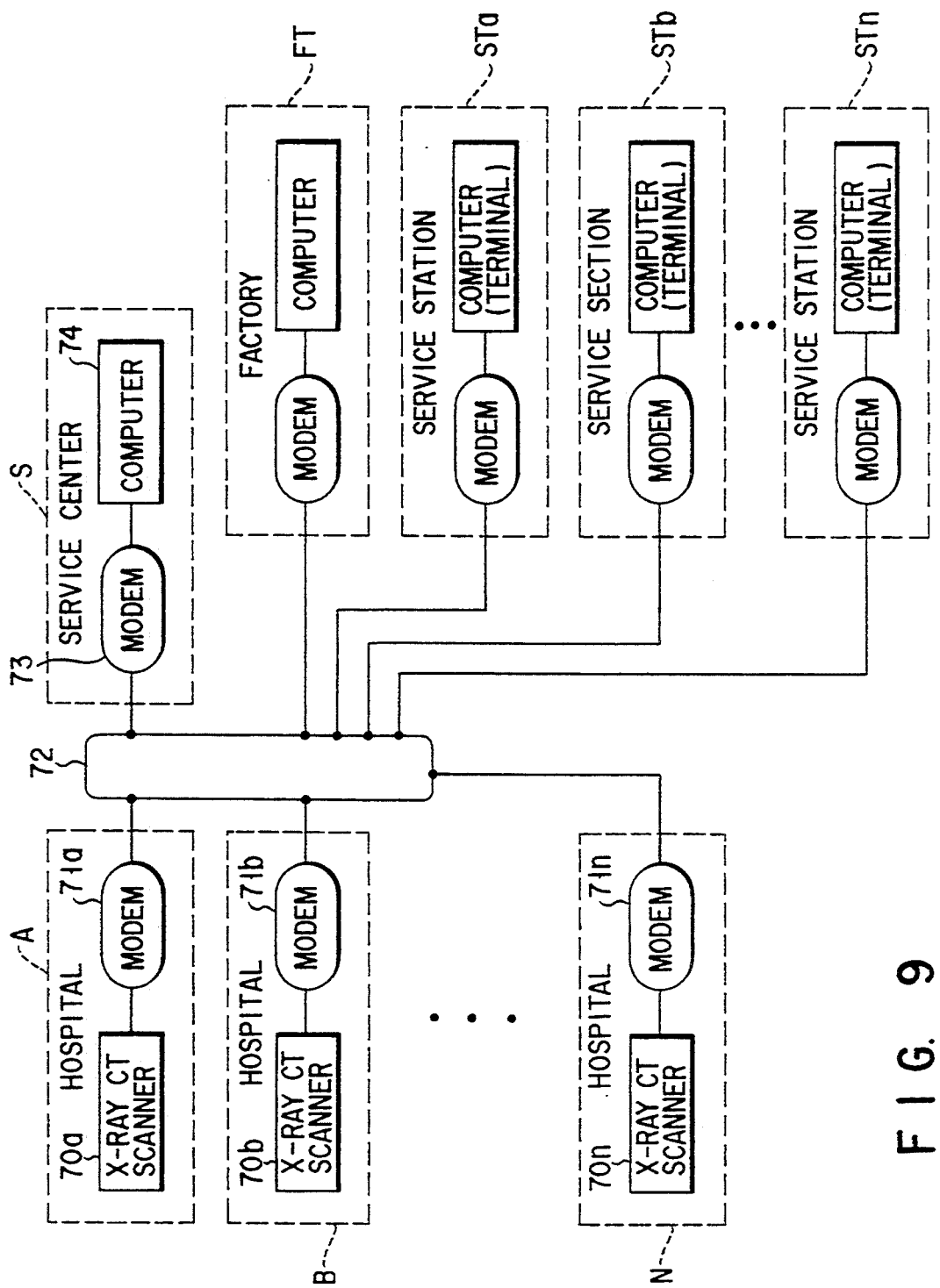
FIG. 9 is a block diagram showing an X-ray apparatus according to a third embodiment of the present invention.

FIG. 9 is a block diagram schematically showing a third embodiment of the present invention.

The third embodiment is directed to remotely diagnosing a plurality of X-ray CT apparatuses. To be specific, the third embodiment is directed to making the servicing/maintenance, etc., of the respective X-ray CT apparatuses by taking signals coming from the X-ray CT apparatuses out of the corresponding rotating frame unit of the X-ray CT apparatus by the use of the signal transmitting means 25 of the first embodiment, grasping the state of the X-ray CT apparatus by the signal obtained and, for example, repairing the respective X-ray CT apparatus depending upon the state of the apparatus. In the third embodiment, an explanation is omitted on the duplicated parts or elements corresponding to those shown in the first embodiment.

In the arrangement shown in FIG. 9, these X-ray CT apparatuses 70a, 70b, ..., 70n are installed on the corresponding sites, such as hospitals A, B, ..., N and their computers are connected via corresponding modems 71a, 71b, ..., 71n to a telephone line 72. The modems 71a, 71b, ..., 71n may be provided separate from the X-ray CT apparatuses 70a, 70b, ..., 70n or each be integrally incorporated into the computer of the X-ray CT apparatus.

A computer 74 of a service center S is connected to the telephone line 72 via a modem 73 in the service center S.

The service center S checks the maintenances of the X-ray CT apparatuses 70a, 70b, ..., 70n of the hospitals A, B, ..., N under centralized control. The service center S can communicate with the respective hospitals A, ..., N over a communication network of the telephone line 72. The service center S has a computer (managing device) 74.

Further, the telephone line 72 is connected to a factory FT manufacturing the X-ray CT apparatuses 70a, 70b, ..., 70n and service stations STa, STb, ..., STn for the servicing and maintenances of the X-ray CT apparatuses 70a, 70b, ..., 70n for communication to be carried out.

Figure 10:
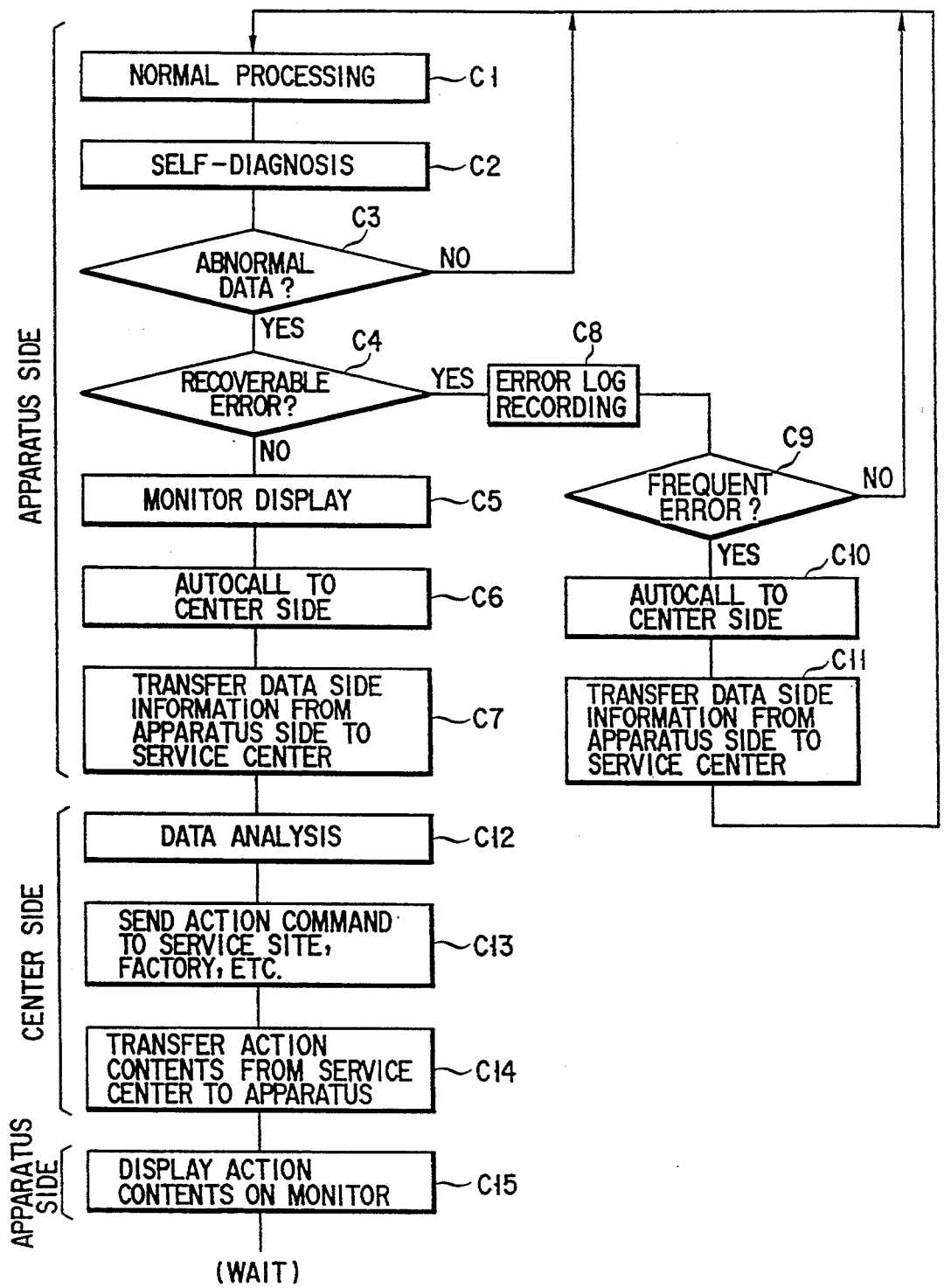
FIG. 10 is a flow chart showing a process from a self-diagnosis to the sending of an action command on the apparatus shown in FIG. 9.

The operation of the X-ray CT apparatus according to the third embodiment of the present invention will be explained below with reference to FIG. 10.

Steps C1 to C11 (FIG. 10) show processings on the X-ray CT apparatus side, that is, on parts of the X-ray CT apparatuses 70a to 70n. First the computer of the X-ray CT apparatus 70a ( ... 70n) performs a normal imaging processing at step C1. At this proper timing upon processing, for example, after the imaging of one patient but before imaging of another patient, step C2 performs a self-diagnostic processing. At step C2, the computer of the X-ray CT apparatus 70a ( ... 70n) runs a stored apparatus-side diagnostic program and a result of diagnosis is obtained. Then control goes to step C3 and the computer of the X-ray CT apparatus 70a ( ... 70n) determines, while under a result of diagnosis, whether or not there is any abnormal function data on the X-ray CT apparatus. At step C3, control is returned back to the normal processing at step C1 when there is no abnormal data and goes to step C4 when there is an abnormal data.

Step C4 determines whether or not the abnormal data found at step C3 is recoverable. If recoverable, subsequent processings are made at steps C5 to C7. At step C5, the abnormal data is displayed as being unrecoverable on the monitor of the X-ray CT apparatus 70a ( ... 70n), representing an expression to the effect that "Error Occurred" and "Now in Contact with Service Center." At step C6, the computer of the X-ray CT apparatus 70a ( ... 70n) starts an autocall processing program and automatically calls the computer 74 of the service center S via the modem 71a ( ... 71n), telephone line 72 and modem 73, thus connecting together the two computers. Then at step S7 abnormal data heretofore collected at the X-ray CT apparatus 70a ( ... 70n) and data, including the X-ray CT apparatus-side information, are transferred to the service center S via the telephone line.

When at step C4 the error data is detected but it is determined as being recoverable, control goes to step C8 and to step C9 after an error log has been recorded. At step C9, it is determined whether or not many errors occur by a processing, such as comparing that frequency with a predetermined threshold value. When, as a result of determination, a specific error is more frequent (YES), an autocall is made to the service center S at step C10 and data transfer is made to the service center S at step C11, thus allowing control to be returned back to the normal processing at step C1 and therefore allowing a parallel processing to be carried out. When at step C9 the error is not frequent (NO) but not yet so specified, control is returned back to step C1 for the normal processing.

Performing a processing, at steps C12 to C14, on the computer 74 of the service center side will be explained below.

At step C12, the service center side receives, for example at all times, data transferred over the telephone line 72 from the X-ray CT apparatus 70a ( ... 70n) and analytically examines the data. At step C13, the service center side delivers, based on the result of analysis at step C12, a command on an action, such as a parts replacement, repairs, to be taken to eliminate an abnormal state of the X-ray CT apparatus 70a ( . . . 70n), that is, delivers the command above to the service site and factory for the purpose as set out above. When the service site and factory constitute a network over the same telephone line, such an action command may be sent through the network or, when there is no such network, the action to be taken is informed to the operator on the service center side over another communication means. At step C14, the data indicating the contents of the action to be taken at step C13 is transferred from the service center S to the X-ray CT apparatus 70a ( . . . 70n) via the telephone line.

Upon receipt of the action contents, the computer on the X-ray CT apparatus 70a ( . . . 70n) displays on its monitor the action contents to the effect that, for example, "A contact has already been made to the service center" and "Please await a call from a servicing engineer on the service station side." and the X-ray CT apparatus 70a ( . . . 70n) is in a ready state.

By so doing, the factory FT, for example, requested for the action taken against the abnormal state at step C13 delivers necessary component parts for repairing/maintenance to the hospital A ( . . . N) or to the corresponding service station STa ( . . . STn). Similarly, the service station STa ( . . . STn) requested for the action taken at step C13 dispatches a servicing engineer to the hospital A ( . . . N).

Even if a failure occurs on the X-ray CT apparatus 70a ( . . . 70n), a prompt repairing operation can be made at any abnormal event without awaiting any contact from the operator on the hospital. As a result, it is possible to reduce the downtime of the X-ray CT apparatus to a minimal possible extent and to hence reduce any adverse influence upon a medical action to a minimal possible extent.

The telephone line may be connected to the service center only at the times of transmitting data and sending a result of action taken to the apparatus side. As shown in FIG. 10, a connection may be set in an available state at steps C7 and C12 to C15.

In the normal processing C1, when the error (abnormal state) occurs, the process after step C4 may be performed by determining whether the error is recoverable. In other word, step C2 is not necessary and the processing such as center autocall by interrupt processing or the like may be performed when the error occurs during normal processing.

Various changes and modifications of the present invention may be made without departing from the spirit and scope of the present invention.

Additional advantages and modifications will readily occur to those skilled in the art. Therefore, the present invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A computed tomography apparatus comprising:
   a rotating frame unit;
   an X-ray high-voltage generating device comprised of at least one component part mounted on said rotating frame unit;
   a measuring device for measuring a signal at each component part of said X-ray high-voltage generating device mounted on said rotating frame unit; and
   signal transmission means for allowing a signal transmission to be made between said X-ray high-voltage generating device and external device means arranged outside said rotating frame unit.

2. The apparatus according to claim 1, wherein said measuring device includes a waveform monitor.

3. The apparatus according to claim 1, wherein said signal transmitting means includes means for transmitting a signal by a light transmission.

4. A computed tomography apparatus comprising:
   a rotating frame unit;
   an X-ray high-voltage generating device having at least one component part mounted on said rotating frame unit and being powered by a source of continuous electrical current external to the rotating frame;
   an operation mechanism operated in a mounted position near said X-ray high-voltage generating device to make at least one of checking and adjustment to the X-ray high-voltage generating device.;
   signal transmitting means for transmitting a signal to said X-ray high-voltage generating device; and
   programmable setting means for programmably setting, under remote control, an operation performed by said operation mechanism on said X-ray high-voltage generating device via said signal transmitting means.

5. The apparatus according to claim 4, wherein said signal transmitting means includes means for transmitting a signal by light transmission.

6. A computed tomography apparatus comprising:
   a rotating frame unit;
   at least one electric device of an optical-system device, a detector and a data acquisition system mounted on said rotating frame unit; and
   a measuring device mounted on said rotating frame unit to measure a signal at each component part of said electric device.

7. The apparatus according to claim 6, further comprising signal transmitting means for allowing a signal transmission to be made between said electric device mounted on said rotating frame unit and external device means mounted outside said rotating frame unit.

8. The apparatus according to claim 7, wherein said signal transmitting means includes means for transmitting a signal by light transmission.

9. The apparatus according to claim 6, wherein said measuring device includes a waveform monitor.

10. A computed tomography apparatus comprising;
    a rotating frame unit;
    at least one electric device of an optical-system device, a detector and a data acquisition system;
    signal transmitting means mounted between said electric device mounted on said rotating frame unit and external device means mounted outside said rotating frame unit; and
    a measuring device for measuring a signal at each component part of said X-ray high-voltage generating device mounted on said rotating frame unit.

11. The apparatus according to claim 10, wherein said signal transmitting means includes means for transmitting a signal by light transmission.

12. The apparatus according to claim 10, wherein said measuring device includes a waveform monitor.

13. The apparatus according to claim 10 further comprising:
- an operation mechanism operated in a mount position of said electric device so as to make at least one of checking and adjustment; and
- programmable setting means for programmably setting, under remote control, an operation performed by said operation mechanism on said electric device via said signal transmission means.

14. The apparatus according to claim 10, wherein said apparatus is installed on a predetermined site and connected to a managing apparatus installed at a center side remote from said predetermined site to manage checking of said apparatus for maintenance and servicing through a communication via a telephone line, said apparatus further comprising:
- self-diagnosing means for running a diagnostic program related to a checking of a self-function;
- means for determining an occurrence of any abnormality of said self-function on the basis of a result of diagnosis by said self-diagnosing means;
- autocall means for automatically connecting a circuit line to said managing apparatus via the telephone line when said determining means determines a presence of an abnormality; and
- information transferring means for transferring a result of diagnosis by said self-diagnosing means and result of determination by said determining means to said center side via the telephone line when the telephone line is connected by said autocall means, wherein
- said managing apparatus includes servicing command informing means for sending a command for a servicing action on the abnormality in said apparatus, on the basis of information transferred from said information transferring means.

15. A remote control system applied to a computed tomography apparatus, which comprises a rotating frame unit and an X-ray high-voltage generating device having at least one component part mounted on said rotating frame unit, installed at a given site and connected to a managing apparatus installed at a center side remote from the site to manage checking of said apparatus for maintenance and servicing through a communication via a telephone line, said system comprising;
- abnormality determining means included in said computed tomography apparatus for determining an occurrence of any abnormality of a self-function;
- autocall means for automatically connecting a circuit line to said managing apparatus via the telephone line when said abnormality determining means determines a presence of the abnormality; and
- information transferring means for transferring a result of diagnosis by said self-diagnosing means and result of determination by said determining means to said center side via said telephone circuit when the telephone line is connected by said autocall means.

16. The system according to claim 15, further comprising servicing command informing means for sending a command for a servicing action on the abnormality in said computerized tomography apparatus, on the basis of information transferred from said information transferring means.

17. The system according to claim 16, further comprising self-diagnosing means included in said computed tomography apparatus for running a diagnostic program related to a checking of a self-function.

18. The system according to claim 15, further comprising a measuring device included in said computed tomography apparatus for measuring a signal at each component part of said X-ray high-voltage generating device mounted on said rotating frame unit.

* * * * *